US005628725A

United States Patent [19]
Ostergard

[11] Patent Number: 5,628,725
[45] Date of Patent: May 13, 1997

[54] SHOULDER STABILIZER METHODS

[75] Inventor: Doak Ostergard, Lincoln, Nebr.

[73] Assignee: The Saunders Group, Inc., Chaska, Minn.

[21] Appl. No.: 407,701

[22] Filed: Mar. 21, 1995

[51] Int. Cl.$^6$ ............................................. A61F 5/00
[52] U.S. Cl. ........................... 602/62; 602/4; 602/20; 602/61
[58] Field of Search ................ 602/4, 5, 20, 61, 602/62; 128/869, 874, 877; 2/44, 45

[56]     References Cited

U.S. PATENT DOCUMENTS

| | | |
|---|---|---|
| 376,872 | 1/1888 | Freeman . |
| 1,466,487 | 8/1923 | Shaffer . |
| 1,991,677 | 2/1935 | Jacks . |
| 2,980,426 | 4/1961 | Johnson . |
| 3,884,403 | 5/1975 | Brewer . |
| 3,906,944 | 9/1975 | Christen . |
| 3,970,316 | 7/1976 | Westmoreland, Jr. . |
| 4,359,221 | 11/1982 | Taylor . |
| 4,446,858 | 5/1984 | Verter . |
| 4,480,637 | 11/1984 | Florek . |
| 4,497,069 | 2/1985 | Braunhut . |
| 4,550,724 | 11/1985 | Berrehail . |
| 4,571,757 | 2/1986 | Zolecki . |
| 4,589,407 | 5/1986 | Koledin et al. . |
| 4,598,703 | 7/1986 | Lindemann . |
| 4,610,244 | 9/1986 | Hammond . |
| 4,644,939 | 2/1987 | Coleman . |
| 4,714,096 | 12/1987 | Guay . |
| 4,735,198 | 4/1988 | Sawa . |
| 4,751,923 | 6/1988 | Marino . |
| 4,784,128 | 11/1988 | Scheuerman ........................ 602/61 |
| 4,905,713 | 3/1990 | Morante . |
| 4,986,266 | 1/1991 | Lindemann . |
| 5,016,650 | 5/1991 | Marlar . |
| 5,063,941 | 11/1991 | White . |
| 5,163,450 | 11/1992 | Cadichon et al. . |
| 5,188,587 | 2/1993 | McGuire et al. . |
| 5,290,218 | 3/1994 | Kilbey . |
| 5,403,268 | 4/1995 | Clement ........................ 602/20 |

FOREIGN PATENT DOCUMENTS 1224099   7/1987   Canada .

OTHER PUBLICATIONS

Catalog, Start™, Sports Therapy and Rehabilitation Technology, Biomet, Inc.®, pp 1–31.
New Products, JOSPT, vol. 18, No. 6, Dec. 1993, p. 707.
Catalog, Pro Catalog, Elbow/Shoulder/Wrist, PRO 450 Shoulder Sleeve.
Catalog, Professional's Choice, Sports Medicine Products, Inc., Shoulder Controller™, A Revolutionary Breakthrough in Sports Medicine.
Catalog SAWA Shoulder Brace, BRACE International.
Advertisement, Training & Conditioning, Brace International, SAWA Shoulder Orthosis.
Advertisement, NATA News, Oct. 1993, MBI Sports Protection Center, p. 22.
C.D. Denison Orthopaedic Appliance Corp., C.D. Denison—Duke Wyre Shoulder Vest.
Catalog, Cadlow Enterprise, The Cadlow Shoulder Stabilizer.

(List continued on next page.)

Primary Examiner—Linda C. Dvorak
Assistant Examiner—Kim M. Lee
Attorney, Agent, or Firm—Mueting, Raasch Gebhardt & Schwappach, P.A.

[57]          ABSTRACT

A shoulder stabilizer system having a chest portion extending around the chest of the athlete, at least one shoulder portion, and an arm portion proximate the shoulder portion for substantially coveting the axilla and the upper arm of the injured shoulder. The garment has an inside surface constructed of a rubberized material for gripping the skin of the athlete and an outside surface constructed of a loop material for engaging with the hook portion of the hook and loop fastener. One or more elastic straps are strategically attached to the garment for limiting or assisting the movement of the shoulder joint. A bifurcated elastic strap may be used for generating complementary forces relative to a single anchor point.

11 Claims, 10 Drawing Sheets

OTHER PUBLICATIONS

Catalog, Boston Brace International, Inc.©, 1993, The Shoulder Subluxation Inhibitor, It Works, pp. 1–12.

Catalog, BENIK, Shoulder and Elbow Supports, Kirkland Shoulder Harness, p. 8.

Catalog, Sporlastic® Biodynamik Biomechanik, New: Shoulder Dislocation Orthotic Device.

Catalog, The Prevent S.O.4 Custom Shoulder Orthoses.

"McDavid™ Sports Medical Products", Catalog of McDavid Knee Guard, Inc., Chicago, IL, p. 13 (Dated 95/96).

"McDavid Universal Shoulder Support", copy of package cover, McDavid Knee Guard, Inc., 1991.

SHOULDER STABILIZER METHODS

FIELD OF THE INVENTION

The present invention is directed to a shoulder stabilizing device for use by athletes, and in particular, a method and apparatus for limiting or assisting movement of a shoulder joint in a wide variety of directions, including external and internal rotation.

BACKGROUND OF THE INVENTION

It is common for athletes with minor shoulder injuries to continue to participate in sports activities. A variety of devices and methods have been developed for managing shoulder injuries to reduce pain and minimize the risk of more serious injury.

It is common for athletes to use tape to immobilize or stabilize a joint, such as the shoulder, against further injury. However, proper taping of the shoulder injury generally requires an experienced trainer or doctor. Additionally, it is difficult for an athlete to self-tape certain injuries, especially shoulder injuries. Perhaps most importantly, tape tends to stretch over time. The initial taping of the injured shoulder places an undue restriction on mobility of the joint. Over a period of time, as the tape stretches and loosens, greater mobility is provided to the athlete at the expense of support to protect the injured shoulder. Finally, removing tape from an injury may be extremely painful to the athlete.

Another approach to stabilizing injured shoulder joints is the use of a removable shoulder brace, such as that disclosed in U.S. Pat. No. 4,735,198 issued to Sawa. Removable shoulder braces are typically directed to preventing abduction of the shoulder joint. For example, elastic straps are wrapped around the upper arm of the athlete and attached to the chest portion of the shoulder brace so as to restrict abduction of the arm. By restricting abduction of the arm, some prior shoulder braces could not be used by certain athletes, such as football receivers, linebackers, and defensive backs. Additionally, overly restrictive shoulder braces have been impractical for basketball and baseball players.

Most prior shoulder braces have been designed for treating specific types of injuries, such as anterior dislocations. Consequently, it is difficult or impossible to use these devices to treat other shoulder injuries. Additionally, a number of these shoulder devices are constructed of materials which slide or slip on the athlete's skin so that it is difficult to control rotational forces on the injured shoulder joint.

SUMMARY OF THE INVENTION

The present invention is directed to a shoulder stabilizer system which can resist or assist movement of an injured shoulder in essentially any direction.

The present shoulder stabilizer system grips the skin of the athlete's upper arm so that external and internal rotational forces can be controlled at the injured shoulder joint. The versatility of the present invention permits the athlete to self-adjust the amount of mobility allowed at the injured shoulder.

The present invention can functionally stabilize, assist or restrict movement of the injured shoulder according to the specific needs of each athlete and application. The assistance or restraint provided by the present invention follows the natural movement of the muscles and joints of the athlete.

The shoulder stabilizer system includes a garment having a chest portion extending around the chest of the athlete, at least one shoulder portion, and an arm portion proximate the shoulder portion for substantially covering the axilla and the upper arm of the injured shoulder to provide additional control and stability. The garment has an inside surface constructed of a rubberized material for gripping the skin of the athlete and an outside surface constructed of a loop material for engaging with the hook portion of the hook and loop fastener. One or more elastic straps can be used for limiting or assisting the movement of the shoulder joint in virtually any direction. Since the garment extends under the axilla, the elastic straps can extend under the axilla of the athlete without creating discomfort. A bifurcated elastic strap may be reed for generating complementary forces relative to a single anchor point.

The garment may also be bilateral so as to cover both shoulder systems simultaneously. Alternatively, an athlete may wear two shoulder stabilizer systems simultaneously on opposite shoulders.

In one embodiment, the shoulder brace is constructed of neoprene laminated on the outer surface with a loop material for engagement with a hook portion of a hook and loop fastener. The neoprene can be perforated to minimize heat buildup.

The shoulder stabilizer system of the present invention is suitable for treating a variety of shoulder injuries such as anterior instabilities, multidirectional instabilities, inferior instabilities, posterior instabilities, rotator cuff strains, shoulder separations, muscle weakness, and muscle strain. The present method controls external and internal rotation of an injured shoulder joint. Additionally, the method of resisting or assisting an injured joint is according to the natural movement of the muscles and the joint.

One method for stabilizing an anterior instability includes attaching an upper and a lower elastic strap to the posterior and lateral aspects of the arm proximate the injured shoulder, so that the proximal ends of the straps extend over the anterior aspect of the arm, toward the axilla. The lower elastic strap is pulled under the axilla, diagonally across the back of the athlete, and over the opposite shoulder. The distal end of the lower strap is theta attached to the chest portion of the garment. The upper elastic strap is pulled under the axilla and generally horizontally across the back of the athlete. The distal end of the upper elastic strap is also attached to the chest portion of the garment. In the preferred embodiment, the distal ends of the upper mad lower elastic straps are attached to the front side of the chest portion so that the athlete can self-adjust the force on each of the straps. The strap configuration serves to pre-load the glenohumeral joint and its capsule in a more posterior position within the joint.

One method for stabilizing a multidirectional instability in an injured shoulder joint includes attaching a first elastic strap to the medial and posterior aspect of the arm proximate the injured shoulder. The first elastic strap is pulled superiorly just distal of the acromion process and diagonally across the chest of the athlete. The distal end of the first elastic strap is attached to the back portion of the garment. A second elastic strap is attached to the medial and anterior aspect of the arm proximate the injured shoulder. The second elastic strap is pulled superiorly and laterally just distal of the acromion process, and diagonally across the athlete's back. The distal end of the second elastic strap is attached to the chest portion of the garment.

One method for stabilizing an inferior instability in a shoulder joint includes attaching a first elastic strap to the medial and posterior aspect of the arm proximate the injured shoulder. The first elastic strap is wrapped anteriorly over the top of the arm and under the axilla. The first elastic strap is then pulled superiorly just distal of the acromion process and diagonally across the chest of the athlete. The distal end of the first elastic strap is attached to the back portion of the garment. A second elastic strap is attached to the medial and anterior aspect of the arm proximate the injured shoulder. The second strap is wrapped posteriorly over the top of the arm and under the axilla. The second elastic strap is pulled superiorly and laterally just distal of the acromion process, and diagonally across the back of the athlete. The distal end of the second elastic strap is attached to the chest portion of the garment.

One method of stabilizing a posterior instability in a shoulder joint includes attaching a first elastic strap to the lateral and anterior aspect of the arm proximate the injured shoulder. The first elastic strap is then pulled in an anterior direction under the axilla and over the posterior and superior aspect of the humeral head. The first elastic strap is then pulled diagonally across the athlete's chest and attached to the back portion of the garment.

One method of providing rotator cuff deceleration in an injured shoulder includes positioning the arm proximate the injured shoulder in an externally rotated position. An elastic strap is attached to the posterior aspect of the arm. The elastic strap is then pulled under the arm and over the acromioclavicular joint, and diagonally across the back of the athlete. The distal end of the elastic strap is then attached to the chest portion of the garment.

The method for providing rotator cuff deceleration simultaneously resists forward rotation of the shoulder joint, which is particularly useful to decelerate the athlete's arm after a throwing motion, and assists the athlete in raising the injured arm. The strap configuration may be reversed to assist the athlete in the throwing motion and to resist raising of the injured arm One method for stabilizing a shoulder separation includes attaching a strap over the acromioclavicular joint to provide a downward force on the head of the joint. A pad may be interposed between the strap and the garment.

One method of treating a muscle strain includes attaching a strap to the medial and posterior aspect of the arm. The strap is pulled superiorly just distal of the acromion process, diagonally across the chest of the athlete, and underneath the axilla of the opposite arm The strap provides a force to assist the anterior chest wall muscles in performing concentric (shortening) contractions.

Definitions as used in this application:

"Acromioclavicular joint" means the joint formed between the acromion process of the scapula and the distal end of the clavicle.

"Acromion process" means the most superior and anterior aspect of the scapula overlying the rotator cuff tendons and joining with the distal end of the clavicle to form the acromioclavicular joint.

"Glenoid fossa" means that aspect of the scapula that serves as the concave joint surface against which the humerus articulates.

"Inferiorly" means a movement in the caudal direction or toward the feet.

"Subluxation or partial dislocation" means the movement of one of the two bones that comprise a joint such that it briefly moves outside of its typical articulation and then back again without the need for external force application or assistance.

"Superiorly" means a movement in the cephalic direction, or toward the head.

BRIEF DESCRIPTION OF THE PREFERRED EMBODIMENT

Figure 1:
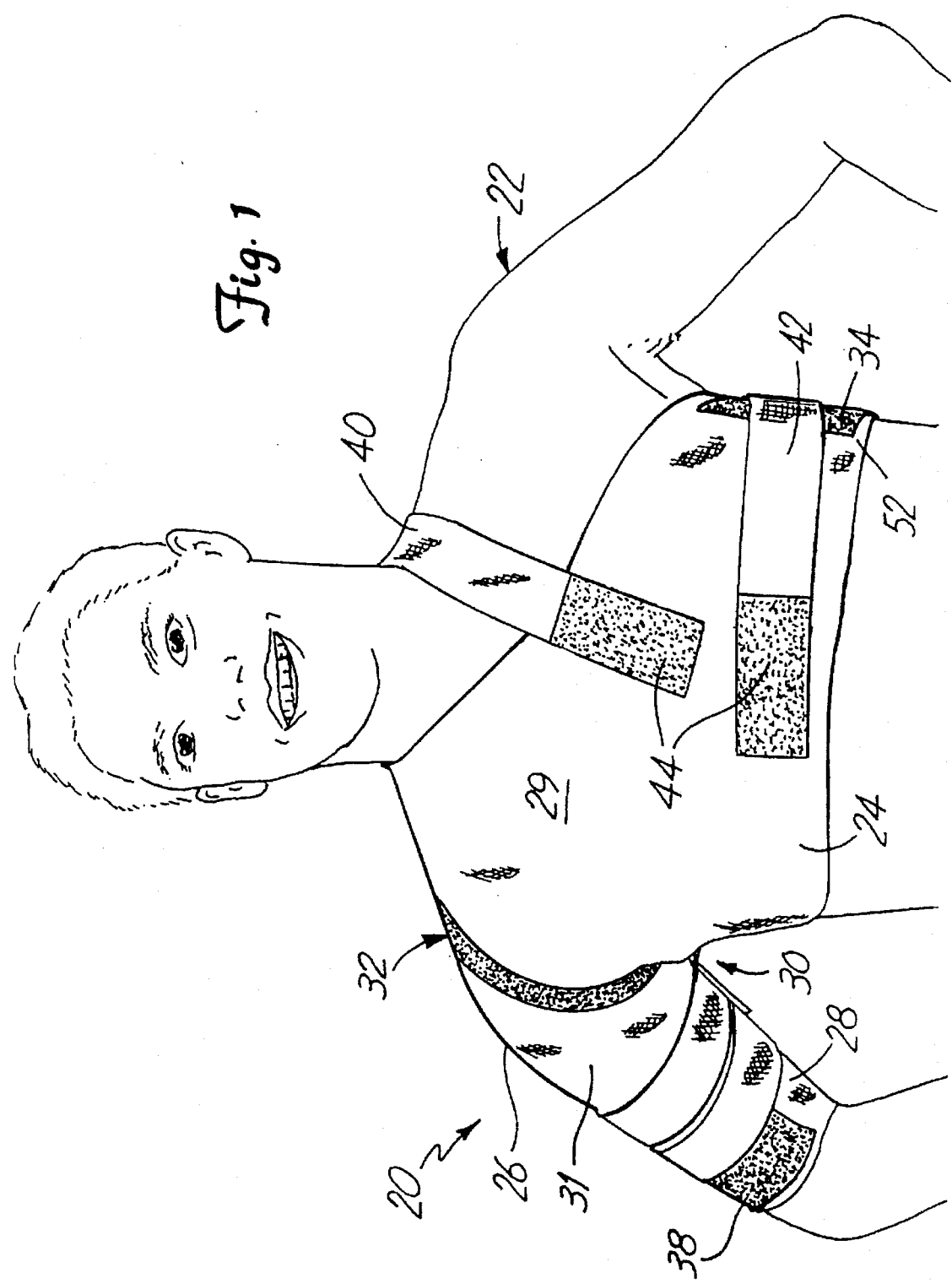
FIG. 1 is a front view of a shoulder stabilizer system in an exemplary configuration for treating an anterior instability.

FIG. 1 illustrates an exemplary shoulder stabilizer system 20 applied to an athlete 22 in a configuration for treating an anterior instability. The shoulder stabilizer system 20 includes garment 29 with a chest portion 24, a shoulder portion 26, and an arm portion 28 for substantially covering the axilla 30 and the upper arm 31 proximate the injured shoulder 32. The shoulder stabilizer system 20 is generally symmetrical so that it can be worn on either shoulder. Distal ends 52 of the chest portion 24 extend around the chest of the athlete 22 and are connected by a fastener 34 on the side opposite the injured shoulder 32. It will be understood that the fastener 34 can be placed in a variety of locations, and that the present invention is not limited to the location of the fastener 34 in the exemplary embodiment of FIG. 1. A closure strap 38 is provided to secure the arm portion 28 to the athlete 22.

The garment portion 29 is preferably constructed of laminated neoprene. The outside of the neoprene is laminated with a hook sensitive loop material. The inside of the garment 29 is unlaminated neoprene, which grips m the skin of the athlete. First and second elastic straps 40, 42 are attached to the upper arm portion 28 and the chest portion 24 of the garment 29 using hook portions 44 of a hook and loop fastener such as Velcro™, as will be discussed below. The neoprene is preferably perforated to minimize heat buildup. Laminated neoprene suitable for this purpose is available from Rubitex Corporation, Bedford, Va.

Figure 2:
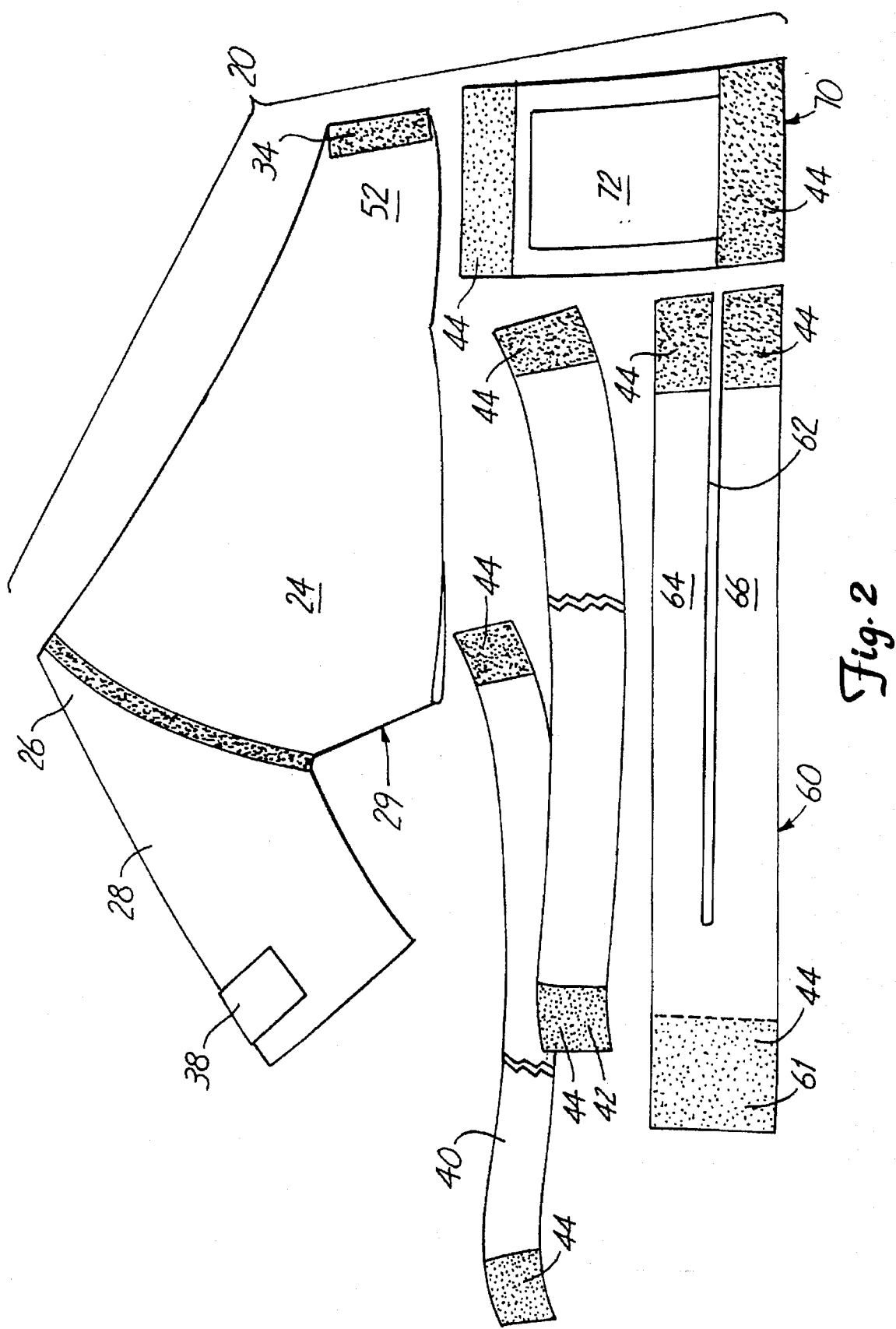
FIG. 2 illustrates exemplary components of a shoulder stabilizer system.

FIG. 2 illustrates an exemplary shoulder stabilizer system 20. The chest portion 24, shoulder portion 26 and arm portion 28 are constructed from a single piece of laminated neoprene. It will be understood that the garment 29 may be constructed in a variety of ways, such as joining sections of laminated neoprene by stitching, heat sealing or some other suitable process. Additionally, the garment 29 may be constructed with a pair of opposing shoulder and arm portions to cover both shoulders of an athlete.

A bifurcated strap 60 is provided for certain therapeutic applications, as will be discussed below. The strap 60 includes an elongated strip of laminated neoprene with a slit 62 along a portion of its longitudinal axis, forming upper and lower straps 64, 66 joined as a common end 61. Hook fasteners 44 are provided on the distal ends of the upper and lower straps 64, 66 and the common end 61 for attachment to the garment 29. An anchor strap 70 having a center pad 72 is also provided, for me in treating shoulder separations. A hook portion 44 of the hook and loop fasteners is provided on both ends of the anchor strap 70. The elastic straps 40, 42, 60, 70 are preferably constructed of laminated neoprene. The outer laminated layer of loop material increases the tensile strength of the material, while the neoprene provides elastic properties. It will be understood that the straps 42, 44, 60, 70 may be constructed of a nonelastic material for certain therapeutic applications.

Figure 3A:
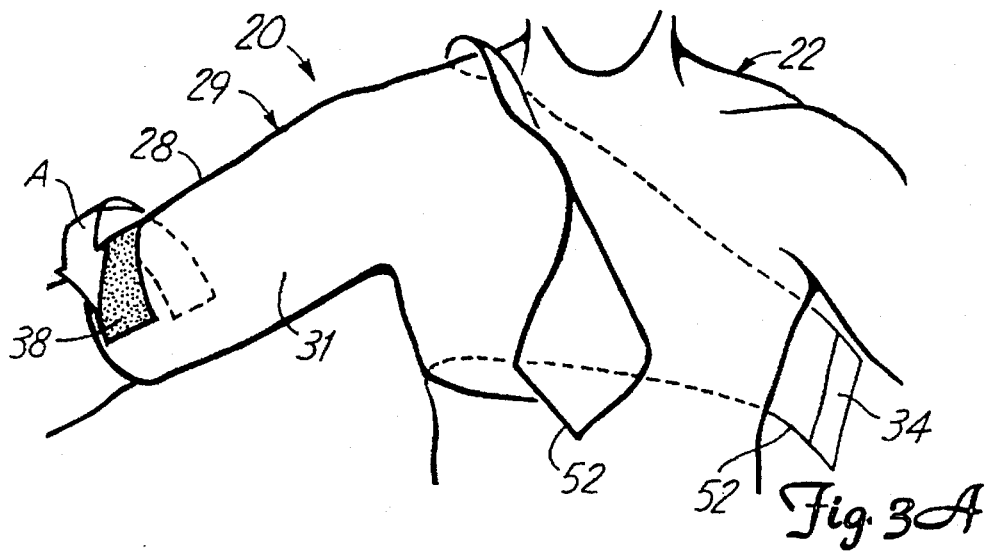
FIGS. 3a–3b illustrate a method of applying a shoulder stabilizer system to an athlete.
Figure 3B:
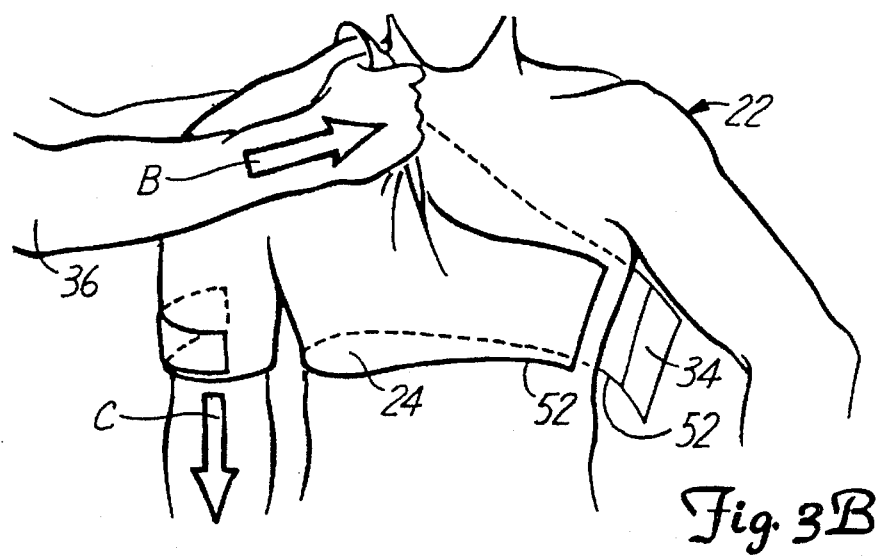
Figure 3C:
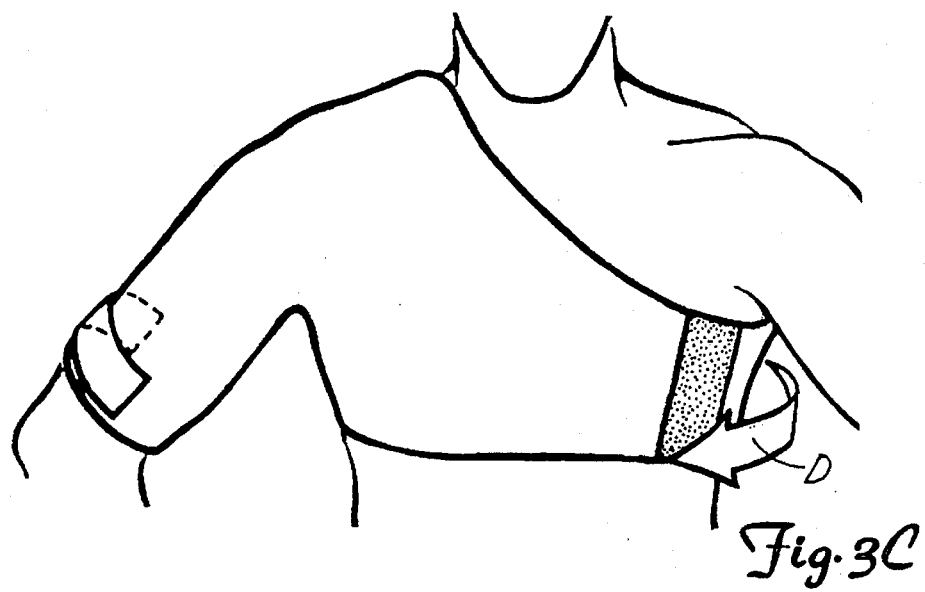

FIGS. 3a–3c illustrate a method of applying a shoulder stabilizer system 20 to an athlete 22. The athlete 22 inserts an arm in the arm portion 28 of the garment 29. The closure strap 38 is pulled in direction "A" to snugly attach the arm portion 28 to the upper arm 31, just above the elbow of the athlete 22. An assistant 36 holds the garment 29 by the chest portion 24 to create a generally horizonal force along the direction "B". Simultaneously, the athlete 22 pushes the upper arm 31 downward along a direction "C" into the garment 29. The closure strap 38 assists in retaining the arm portion 28 relative to the upper arm 31. The forces "B" and "C" assist in attaching the garment 29 to the skin of the athlete 22 in a stretched configuration. The stretched configuration enhances the engagement of the inner surface of the garment 29 with the skin of the athlete 22, so as to minimize slippage of the garment 29.

Distal ends 52 of the garment 29 are then wrapped around the chest of the athlete 22. Fastener 34 is pulled along the direction "D" to provide a comfortable but snug fit. In this configuration, the shoulder stabilizer system 20 can be used to treat multiple injuries, including anterior instabilities, multidirectional instabilities, inferior instabilities, posterior instabilities, rotator cuff decelerations, shoulder separations, and muscle strains.

Figure 4A:
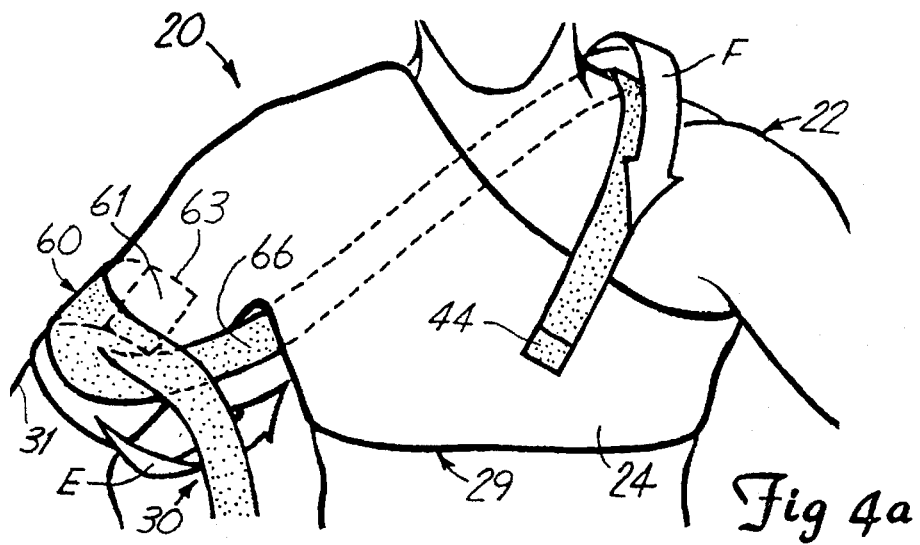
FIGS. 4a–4c illustrate an exemplary configuration of a shoulder stabilizer system for treating an anterior instability.
Figure 4B:
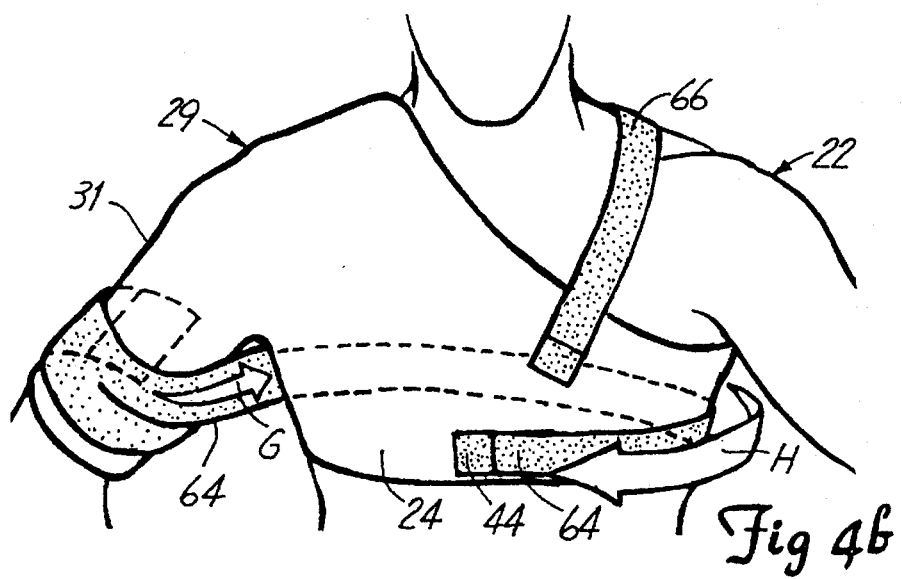
Figure 4C:
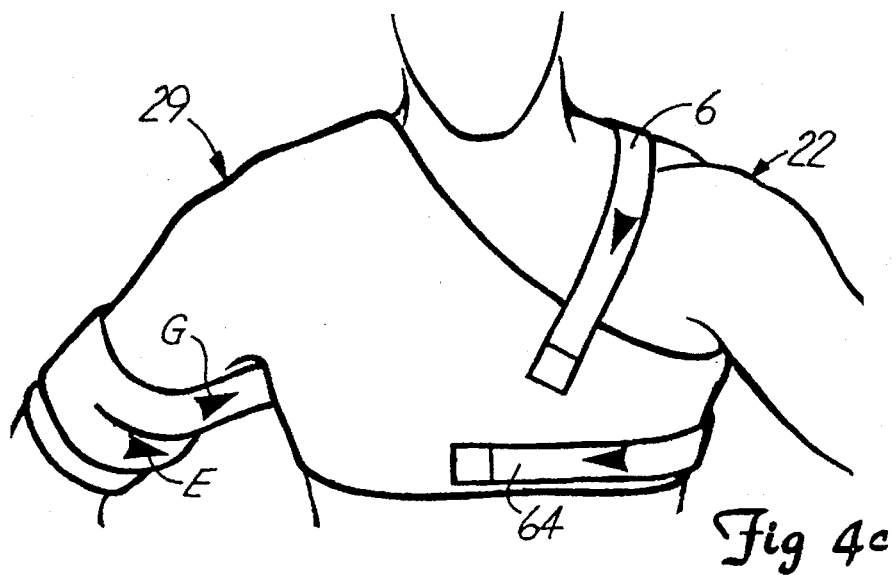

FIGS. 4a–4c illustrate a configuration of the shoulder stabilizer system 20 for treating an anterior instability. Anterior instabilities of the shoulder arise when the humeral head travels or translates toward or outside of the anterior aspect of the glenoid fossa and rim. The common end 61 of the bifurcated strap 60 is attached to the posterior and lateral aspect of the upper arm 31 at a location 63. As shown in FIG. 4a, the lower strap 66 is pulled over the top of the upper arm 31, under the axilla 30 along the direction "E", diagonally across the back of the athlete 22. The distal end of the strap 66 is pulled over the opposite shoulder along a direction "F" and attached to the chest portion 24 of the garment 29 using fastener 44. As shown in FIG. 4b, the upper strap 64 is pulled over the top of the upper arm 31, under the axilla along the direction "G", generally horizontally across the back of the athlete 22. The distal end of the upper strap 66 is wrapped around the waist of the athlete along direction "H" and attached to the chest portion 24 using fastener 44. The lines of pull E, F, and G of the bifurcated strap 60 maximizes the force generated, while conforming the strap 60 to the body. In this configuration, the upper and lower straps 64, 66 can be adjusted by the athlete 22 without assistance. However, it will be understood that the upper and lower straps 64, 66 may be attached to the garment 29 along the back of the athlete.

As shown in FIG. 4c, the straps 64, 66 are configured to maintain constant posterior tension on the humeral head within the shoulder socket. Both forces "E" and "G" are directed posteriorly to dynamically control and limit external rotation, abduction, and flexion of the injured shoulder 32. The straps 64, 66 serve to pre-load the glenohumeral joint and its capsule in a more posterior position within the joint, thereby reducing strain on the anterior aspect of the joint capsule.

Figure 5A:
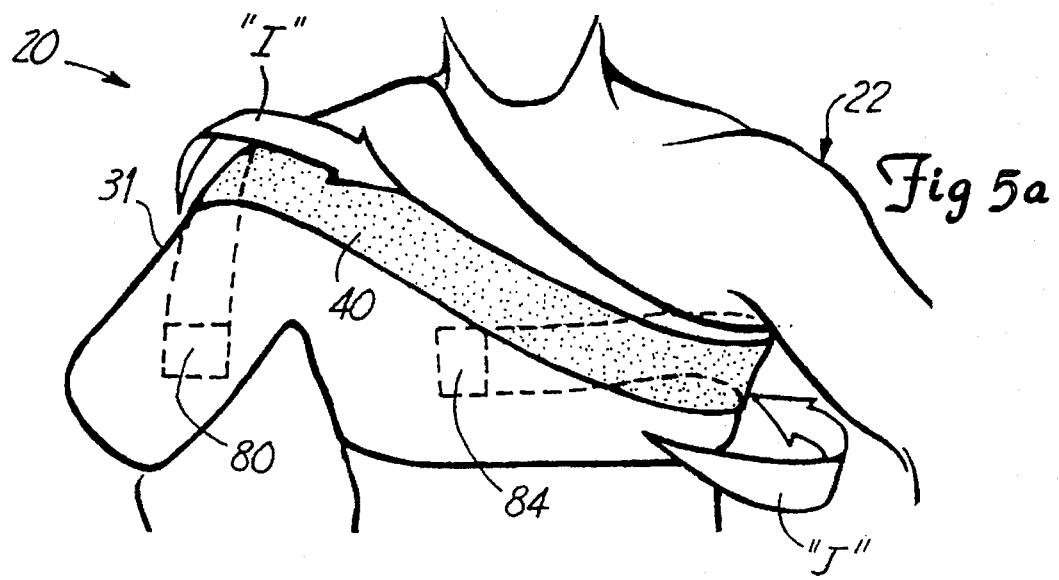
FIGS. 5a–5c illustrate an exemplary configuration of a shoulder stabilizer system for treating a multidirectional instability.
Figure 5B:
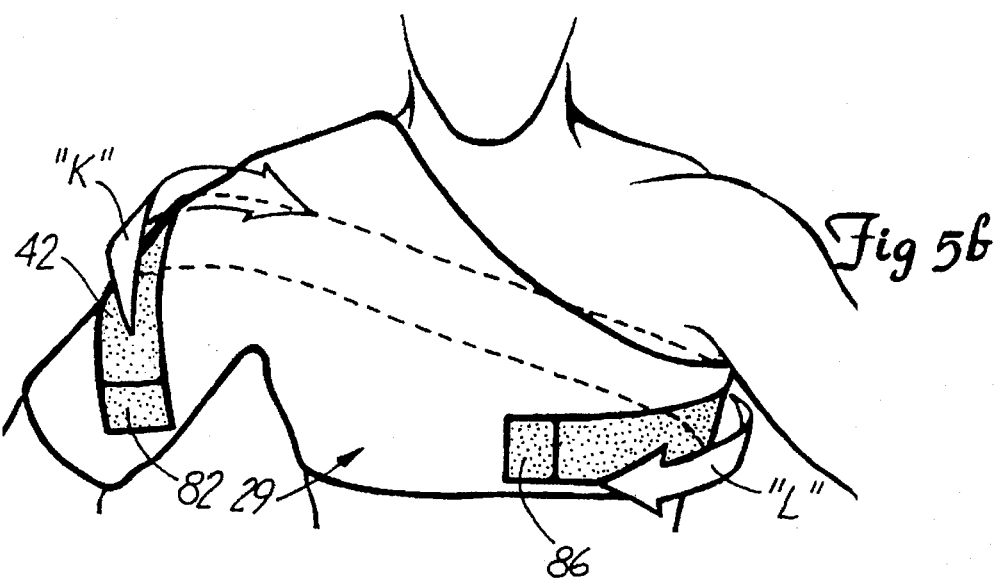
Figure 5C:
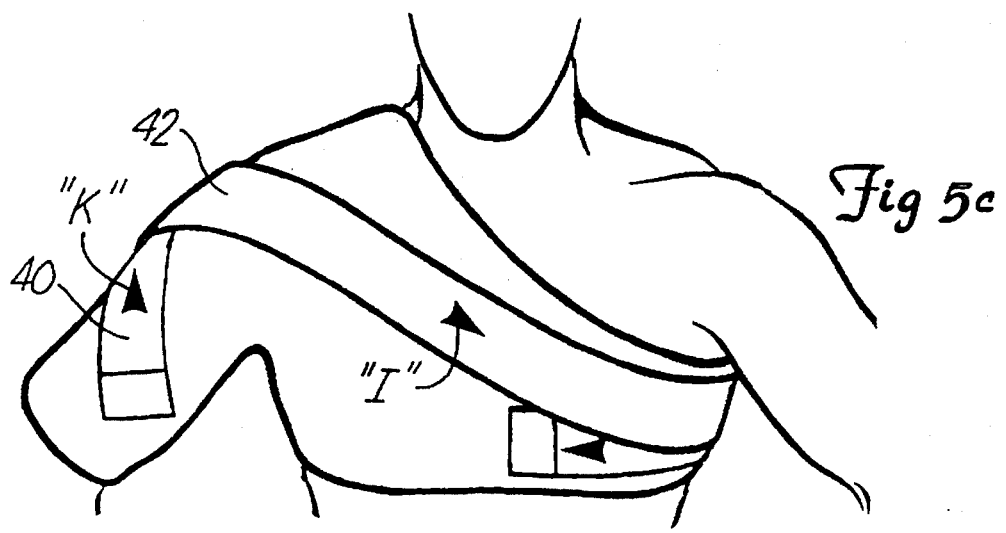

FIGS. 5a–5c illustrate a configuration of a shoulder stabilizer system 20 for treating a multi-directional instability. A multi-directional instability occurs when the shoulder capsule allows excessive movement or mobility of the humeral head within the shoulder socket in two or more directions. As illustrated in FIG. 5a, one end of the first elastic strap 40 is attached to the medial and posterior aspect of the upper arm 31 at a location 80. The strap 40 is pulled superiorly just distal of the acromion process along a direction "I". The strap 40 extends diagonally across the chest of the athlete 22, trader the axilla of the opposite arm along a direction "J". The distal end of the strap 40 is attached to the garment 29 along the back of the athlete 22 at location 84. As illustrated in FIG. 5b, the second strap 42 is attached to the medial anterior aspect of the upper arm 31 at the location 82. The strap 42 is pulled superiorly and laterally just distal of the acromion process along a direction "K". The strap 42 then extends diagonally across the back of the athlete, under the axilla of the opposite arm, where it is attached to the garment 29 at the location 86. As illustrated in FIG. 5c, the straps 40, 42 create forces "I" and "K" which limit internal and external rotation, flexion and abduction of the shoulder, while providing constant elevation of the humeral head within the shoulder socket.

Figure 6A:
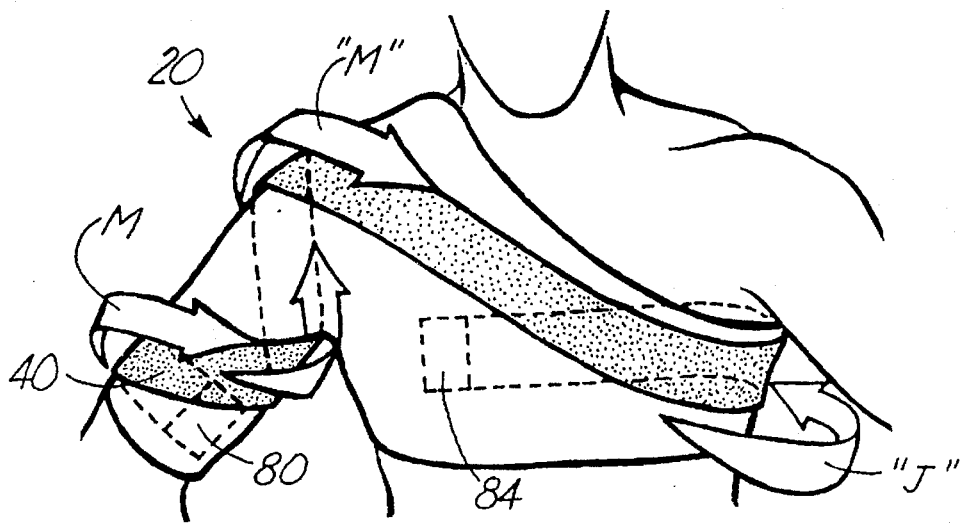
FIGS. 6a–6c illustrate an exemplary configuration of a shoulder stabilizer system for treating an inferior instability.
Figure 6B:
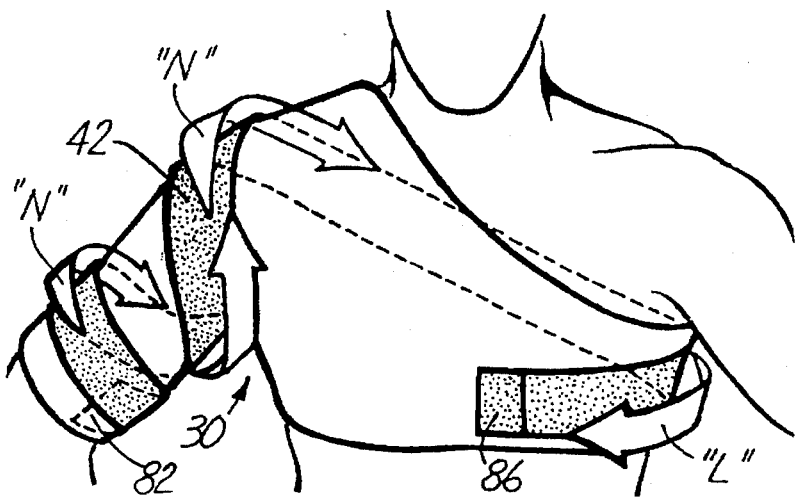
Figure 6C:
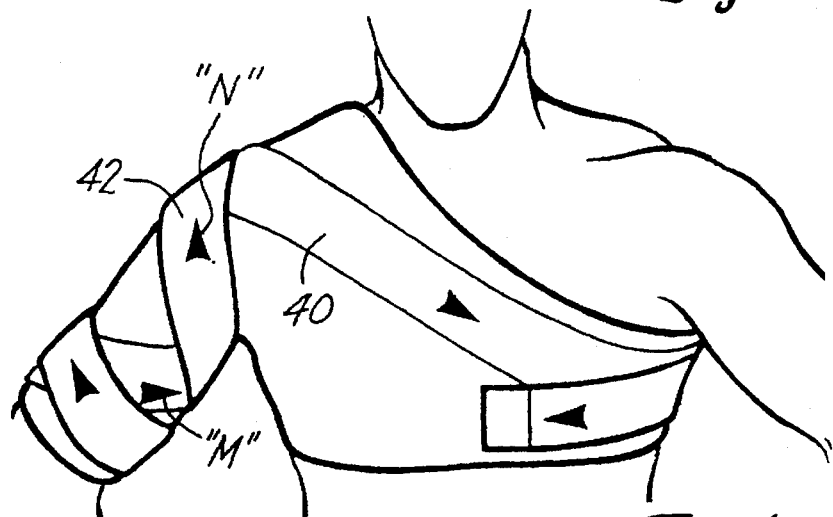

FIGS. 6a–6c illustrate a configuration of the shoulder stabilizer system 20 for treating an inferior instability. An inferior instability occurs when there is a tendency for the humeral head to travel inferiorly or downward within the glenoid fossa. As illustrated in FIG. 6a, the first elastic strap 40 is attached to the medial and posterior aspect of the arm at a location 80. The strap 40 is then spiraled around the front of the arm under the axilla, and over the acromioclavicular joint along the direction "M". The strap then extends diagonally across the chest of the athlete, and around the back along the direction "J". The distal end of the strap 40 is attached to the garment 29 at a location 84.

As illustrated in FIG. 6b, the second elastic strap 42 is attached to the medial anterior aspect of the arm at a location 82. The strap 42 is wrapped around the back of the arm and under the axilla 30 along the direction "N". The strap 42 extends diagonally across the back of the athlete, under the axilla of the other arm along a direction "L", where it is attached to the garment 29 a location 86. As illustrated in FIG. 6c, the straps 40, 42 create forces "M" and "N" which elevate the position of the humeral head within the glenoid fossa to limit the tendency of gravity or external forces to pull the humeral head downward or inferiorly.

Figure 7A:
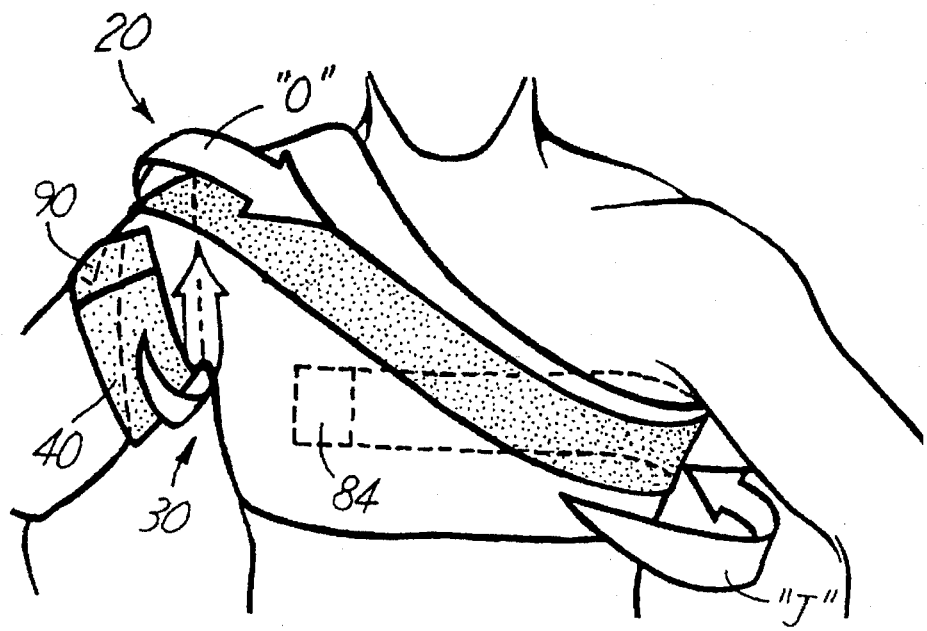
FIGS. 7a and 7b illustrate a configuration of a shoulder stabilizer system for treating a posterior instability.
Figure 7B:
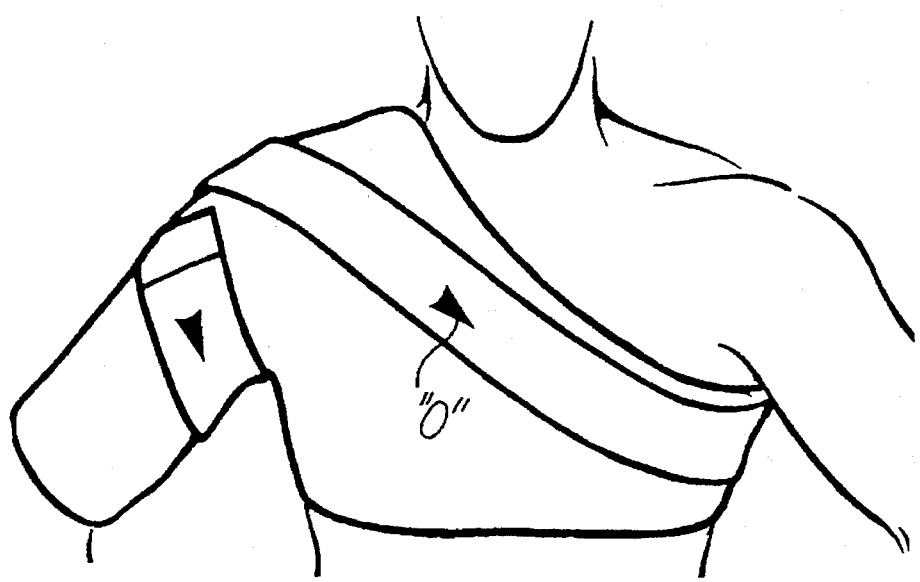

FIGS. 7a and 7b illustrate a shoulder stabilizer system 20 configured to treat a posterior instability. A posterior instability occurs when the humeral head travels or translates posteriorly within the glenoid fossa. As illustrated in FIG. 7a, elastic strap 40 is attached to the lateral and anterior aspect of the upper arm 31 at a location 90. The strap 40 is pulled under the axilla 30 along a direction "O" and over the posterior and superior aspects of the humeral head. The strap 40 then extends diagonally across the chest of the athlete, under the axilla of the opposite arm along a direction "J", where it is attached to the garment 29 at a location 84. As illustrated in FIG. 7b, the strap 40 provides additional tissue support and tension over the posterior aspect of the joint along the force "O" in an attempt to restrain posterior subluxation or dislocation.

Figure 8A:
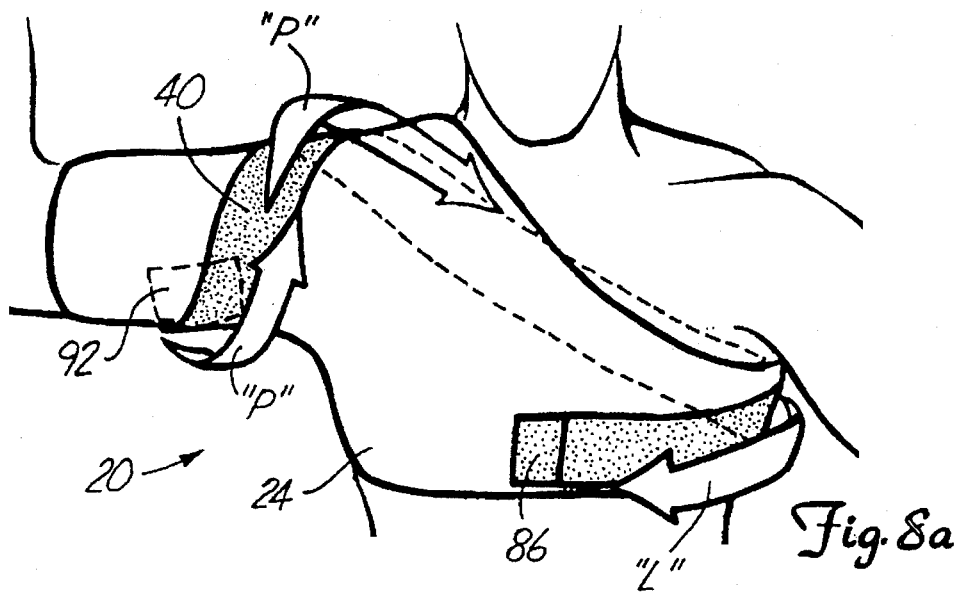
FIGS. 8a–8c illustrate a configuration of a shoulder stabilizer system for assisting in rotator cuff deceleration.
Figure 8B:
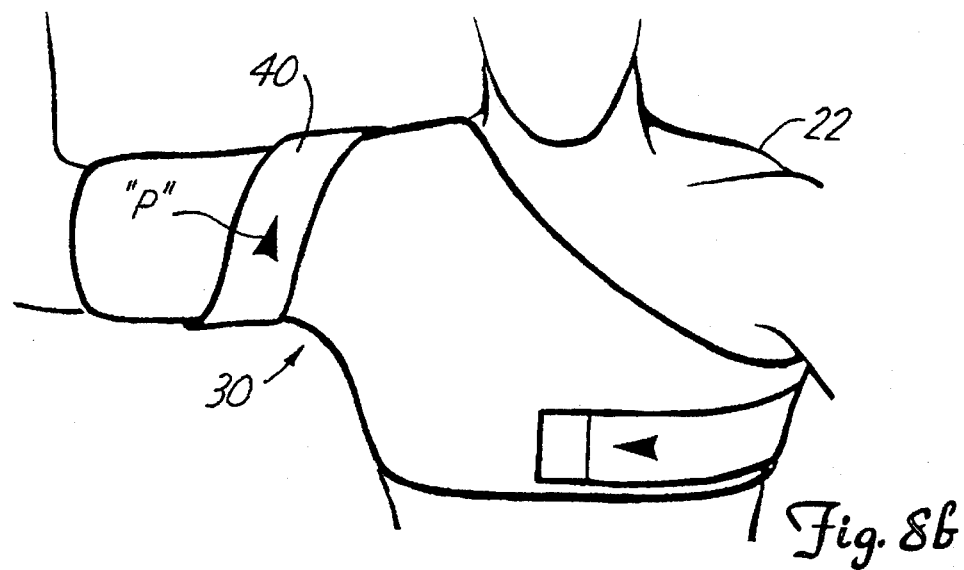
Figure 8C:
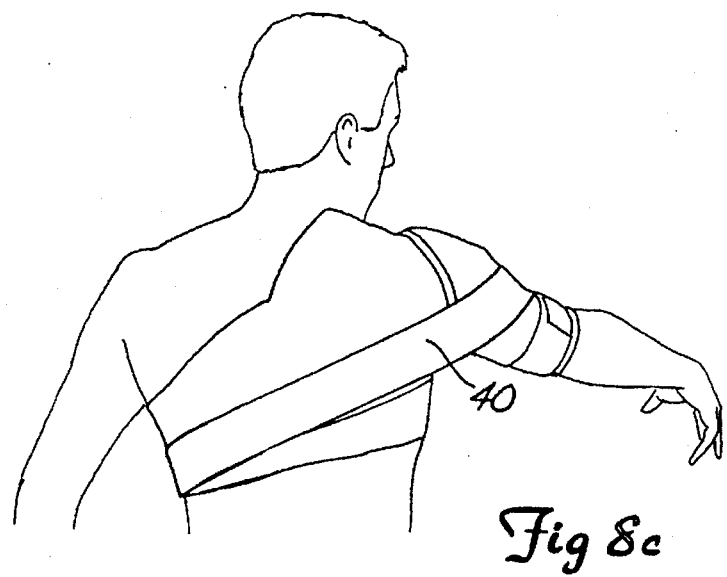

FIGS. 8a–8c illustrate a shoulder stabilizer system 20 configured for artificially creating a rotator cuff deceleration. Rotator cuff deceleration occurs naturally in the body when the rotator cuff musculature is functioning optimally. In cases of excessive wear and tear on the rotator cuff muscle group or when tendinitis or bursitis are present, the functioning of the rotator cuff in decelerating the arm is reduced. This deceleration occurs most commonly at the end phase of a throw to slow the arm down after release of a ball.

The athlete's arm is located in an externally rotated position as illustrated in FIG. 8a. An elastic strap 40 is attached to the posterior aspect of the athlete's arm at a location 92. The strap 40 is pulled under the arm along the direction "P" and over the acromioclavicular joint. The strap 40 then extends diagonally across the back of the athlete, under the axilla of the opposite arm along a direction "L", where it is attached to the garment 29 at a location 86. As illustrated in FIG. 8b, the rotational force "P" of the strap 40 assists the athlete move the arm into an externally rotated position. When the athlete 22 extends the arm forward, as illustrated in FIG. 8c, the strap 40 provides resistance (deceleration) to that internal rotation of the shoulder joint.

It will be understood that the strap 40 may be wrapped in a direction opposite to "P" so as to assist the forward motion of the arm illustrated in FIG. 8c. For example, the athlete's arm may be located in an internally rotated forward position as illustrated in FIG. 8c. An elastic strap 40 is then attached to the posterior aspect of the athlete's arm at a location 92. The strap 40 is pulled over the arm and the acromioclavicular joint. The strap 40 then extends diagonally across the chest of the athlete, under the axilla of the opposite arm along a direction opposite to "L", where it is attached to the garment 29 at a back of the athlete. The elastic force of the strap 40 will assist the athlete move the arm into an internally rotated position. When the athlete 22 extends the arm forward, as illustrated in FIG. 8c, the strap 40 will provide assistance (acceleration) to that internal rotation of the shoulder joint.

Figure 9A:
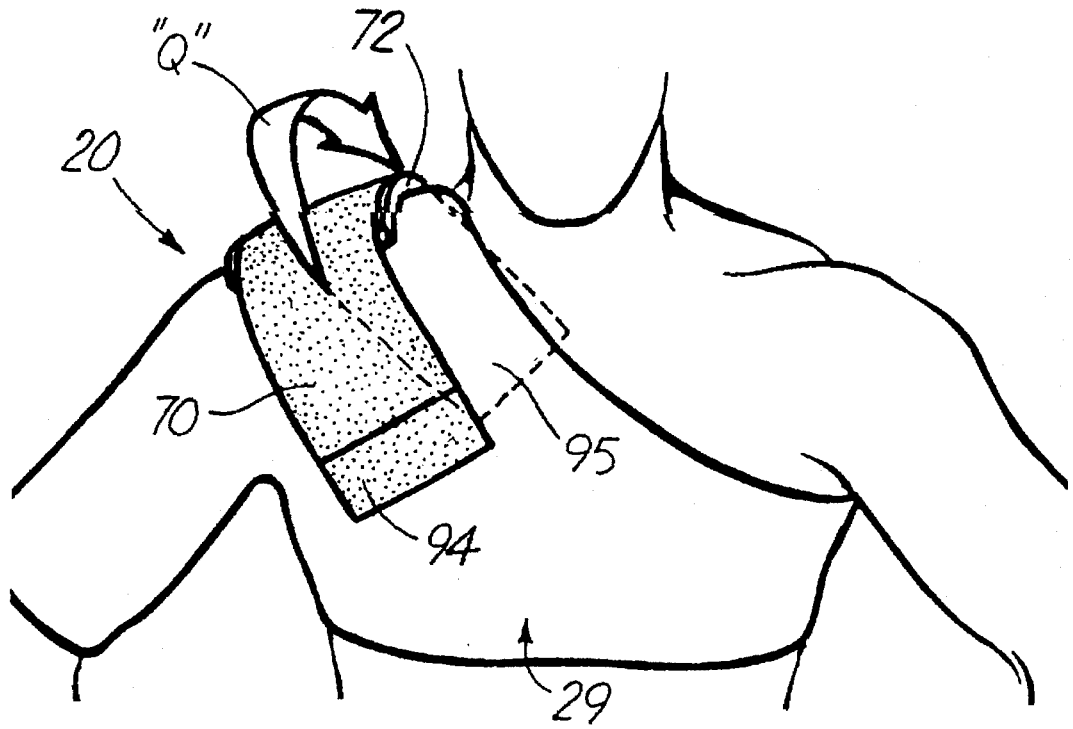
FIGS. 9a and 9b illustrate a configuration of a shoulder stabilizer system for treating a shoulder separation.
Figure 9B:
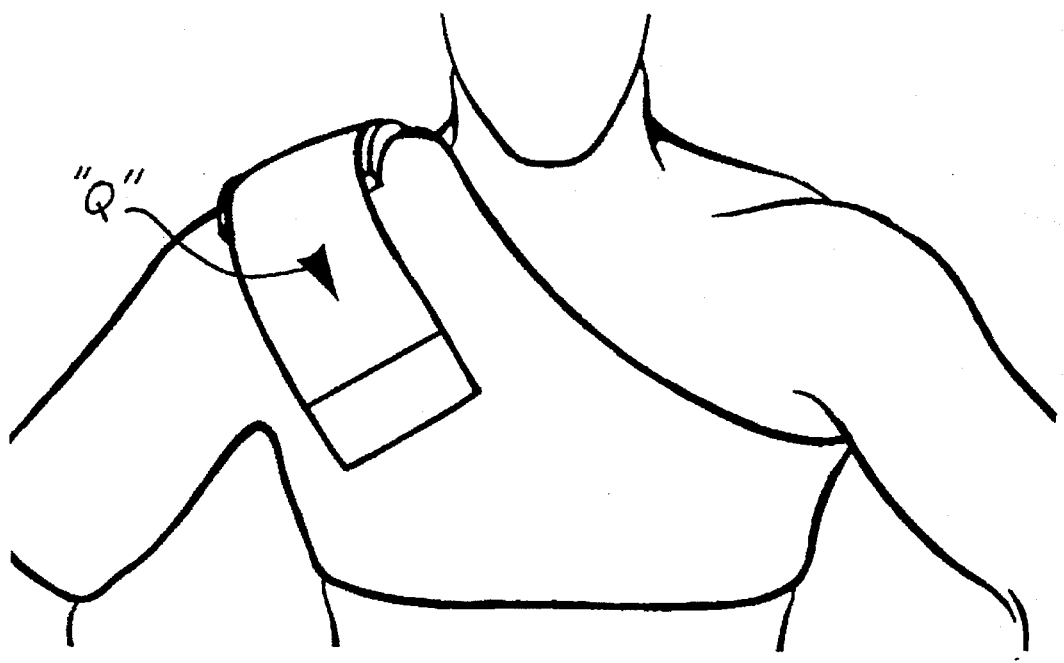

FIGS. 9a and 9b illustrate a shoulder stabilizer system 20 configured to treat a shoulder separation. Shoulder separations occur when the ligaments between the clavicle and scapula become traumatized. The purpose of this strap configuration for shoulder separations is to provide some approximation between these two skeletal elements so as to increase the potential for healing of the ligaments and to maintain stability of the upper quarter. Anchor strap 70 is positioned so that the pad 72 is located proximate the acromioclavicular joint. The distal ends 94, 95 of the anchor strap 70 are attached to the garment 29 so as to provide a downward force "Q" over the acromioclavicular joint (not shown) as shown in FIG. 9b.

Figure 10A:
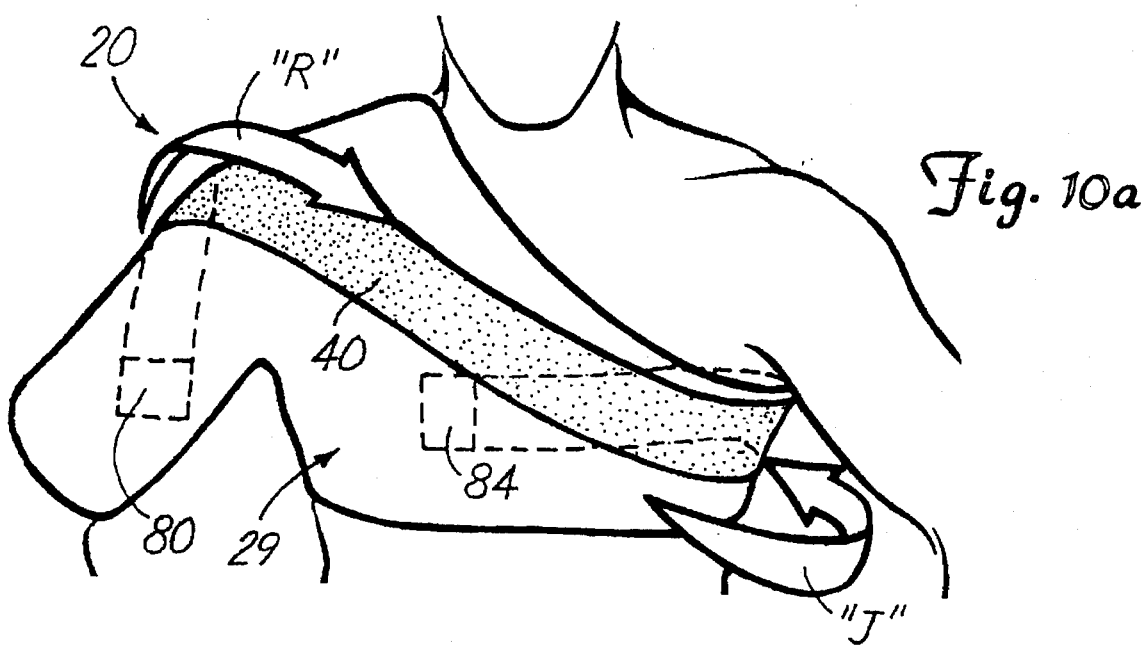
FIGS. 10a and 10b illustrate a configuration of a shoulder stabilizer system for treating a muscle strain.
Figure 10B:
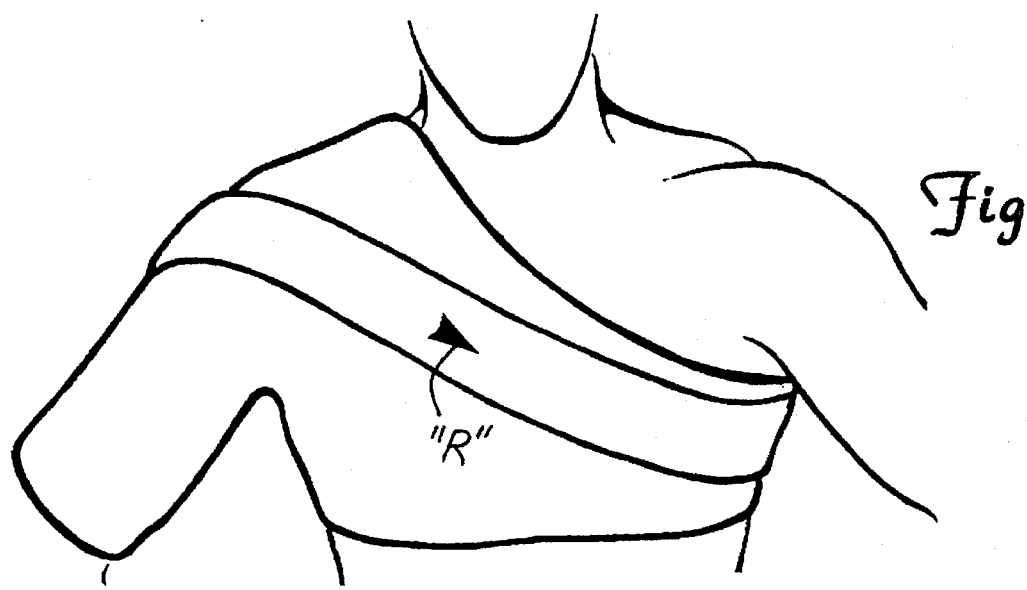

FIGS. 10a and 10b illustrate a shoulder stabilizer system 20 configured for treating muscle strains. Muscle strains occur when muscles such as the pectoral group have been damaged through excessive stretching, contraction or contusion. Elastic strap 40 is attached to the medial and posterior aspect of the arm at a location 80. The strap is pulled superiorly just distal of the acromion process along a direction "R". The strap 40 then extends diagonally across the chest of the athlete, underneath the axilla of the opposite arm along a direction "J", where it is attached to the garment 29 at a location 84. The configuration of the strap 40 provides a force "R" to assist the anterior chest wall muscles in performing concentric (shortening) contractions. The strap 40 also helps to control excessive stretching of the strained muscles.

Although the invention has been described with respect to specific preferred embodiments, it should be appreciated that other embodiments utilizing the concept of the present invention are possible without departing from the scope of the invention. The invention is not intended to be limited to the specific embodiments; rather the invention is defined by the claims and equivalents thereof.

What is claimed is:

1. A method for stabilizing an anterior instability in an injured shoulder of an athlete, comprising the steps of:

applying a garment to an athlete, the garment having a chest portion adapted to extend around the chest of the athlete, a shoulder portion and an arm portion proximate the shoulder portion adapted to substantially cover the axilla and the upper arm of the injured shoulder, a portion of an outer surface of the garment being constructed of a loop material for engagement with a hook portion of a hook and loop fastener;

attaching an upper and a lower elastic strap to the posterior and lateral aspect of the arm portion proximate the injured shoulder so that distal ends of the straps extend over the top of the arm toward the anterior portion of the athlete;

pulling the lower elastic strap under the axilla of the injured shoulder, diagonally across the back of the athlete, and over the opposite shoulder;

attaching the distal end of the lower elastic strap to the chest portion of the garment;

pulling the upper elastic strap under the axilla and generally horizontally across the back of the athlete; and attaching the distal end of the upper elastic strap to the chest portion of the garment to maintain a generally constant posterior tension on a humeral head within a shoulder socket of the injured shoulder.

2. The method of claim 1 wherein the garment has an inside surface constructed of a rubberized material for gripping the skin of the athlete.

3. The method of claim 1 wherein the upper and the lower elastic strap comprises a single bifurcated strap.

4. A method for stabilizing a multi-directional instability in an injured shoulder of an athlete, comprising the steps of:

applying a garment to an athlete, the garment having a chest portion adapted to extend around the chest of the athlete, a shoulder portion and an arm portion proximate the shoulder portion adapted to substantially cover the axilla and the upper arm of the injured shoulder, a portion of an outer surface of the garment being constructed of a loop material for engagement with a hook portion of a hook and loop fastener;

attaching a first elastic strap to the medial and posterior aspect of the arm portion proximate the injured shoulder;

pulling the first elastic strap superiorly just distal of the acromion process and diagonally across the chest of the athlete;

attaching the distal end of the first elastic strap to the chest portion of the garment creating a force to limit external rotation of the shoulder;

attaching a second elastic strap to the arm portion proximate the medial and anterior aspect of the arm of the injured shoulder;

pulling the second elastic strap superiorly and laterally just distal of the acromion process, and diagonally across the back of the athlete; and attaching the distal end of the second elastic strap to the chest portion of the garment creating a force to limit internal rotation of the shoulder and to provide generally constant elevation of a humeral head within a shoulder socket.

5. The method of claim 4 wherein the garment has an inside surface constructed of a rubberized material for gripping the skin of the athlete.

6. A method for stabilizing an inferior instability in an injured shoulder of an athlete, comprising the steps of:

applying a garment to an athlete, the garment having a chest portion adapted to extend around the chest of the athlete, a shoulder portion and an arm portion proximate the shoulder portion adapted to substantially cover the axilla and the upper arm of the injured shoulder, a portion of an outer surface of the garment being constructed of a loop material for engagement with a hook portion of a hook and loop fastener;

attaching a first elastic strap to the medial and posterior aspect of the arm portion proximate the injured shoulder;

wrapping the first elastic strap over the top of the arm and under the axilla of the injured shoulder;

pulling the first elastic strap superiorly just distal of the acromion process and diagonally across the chest of the athlete;

attaching the distal end of the first elastic strap to the chest portion of the garment;

attaching a second elastic strap to the arm portion proximate the medial and anterior aspect of the arm of the injured shoulder;

wrapping the second elastic strap around the back of the arm and under the axilla of the injured shoulder;

pulling the second elastic strap superiorly and laterally just distal of the acromion process, and diagonally across the back of the athlete; and attaching the distal end of the second elastic strap to the chest portion of the garment to elevate a posterior of a humeral head within a glenoid fossa of the injured shoulder.

7. The method of claim 6 wherein the garment has an inside surface constructed of a rubberized material for gripping the skin of the athlete.

8. A method for stabilizing a posterior instability in an injured shoulder of an athlete, comprising the steps of:

applying a garment to an athlete, the garment having a chest portion adapted to extend around the chest of the athlete, a shoulder portion and an arm portion proximate the shoulder portion adapted to substantially cover the axilla and the upper arm of the injured shoulder, a portion of an outer surface of the garment being constructed of a loop material for engagement with a hook portion of a hook and loop fastener;

attaching a first elastic strap to the lateral and anterior aspect of the arm portion proximate the injured shoulder;

pulling the first elastic strap in the anterior direction under the axilla of the injured shoulder and over the posterior and superior aspect of the humeral head;

pulling the first elastic strap diagonally across the chest of the athlete; and attaching the distal end of the first elastic strap to the chest portion of the garment to restrain posterior dislocation of the injured shoulder.

9. The method of claim 8 wherein the garment has an inside surface constructed of a rubberized material for gripping the skin of the athlete.

10. A method of providing rotator cuff deceleration in an injured shoulder of an athlete, comprising the steps of:

applying a garment to an athlete, the garment having a chest portion adapted to extend around the chest of the athlete, a shoulder portion and an arm portion proximate the shoulder portion adapted to substantially cover the axilla and the upper arm of the injured shoulder, a portion of an outer surface of the garment being constructed of a loop material for engagement with a hook portion of a hook and loop fastener;

positioning the arm proximate the injured shoulder in an externally rotated position;

attaching an elastic strap to the arm portion proximate the posterior aspect of the arm;

pulling the first elastic strap under the arm, over the acromioclavicular joint, and diagonally across the back of the athlete; and attaching the distal end of the first elastic strap to the chest portion of the garment to provide resistance to internal rotation of the injured shoulder.

11. The method of claim 10 wherein the garment has an inside surface constructed of a rubberized material for gripping the skin of the athlete.

* * * * *